(12) United States Patent
Tanaka et al.

(10) Patent No.: US 8,994,801 B2
(45) Date of Patent: Mar. 31, 2015

(54) IMAGE PROCESSING APPARATUS

(71) Applicant: Olympus Medical Systems Corp., Tokyo (JP)

(72) Inventors: Kenichi Tanaka, Hino (JP); Hirokazu Nishimura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/955,594

(22) Filed: Jul. 31, 2013

(65) Prior Publication Data
US 2014/0028821 A1 Jan. 30, 2014

Related U.S. Application Data

(63) Continuation of application No. PCT/JP2012/080679, filed on Nov. 28, 2012.

(30) Foreign Application Priority Data

Mar. 21, 2012 (JP) ................. 2012-064195

(51) Int. Cl.
*A62B 1/04* (2006.01)
*A61B 1/00* (2006.01)
(Continued)

(52) U.S. Cl.
CPC ............. *A61B 1/04* (2013.01); *A61B 1/00009* (2013.01); *A61B 1/0002* (2013.01); *A61B 1/05* (2013.01);
(Continued)

(58) Field of Classification Search
CPC .... A61B 1/00009; A61B 1/0002; A61B 1/04; A61B 1/05; A61B 1/0669; G06T 7/00
USPC ............. 348/65, 68, 74, 71, 76, 75; 382/128, 382/199, 266, 224; 600/103, 410, 109, 432, 600/160, 118
See application file for complete search history.

(56) References Cited

U.S. PATENT DOCUMENTS 6,960,165 B2 * 11/2005 Ueno et al. .................... 600/181
8,144,993 B2 * 3/2012 Nishimura et al. ........... 382/199
(Continued)

FOREIGN PATENT DOCUMENTS

EP 2 294 964 A1 3/2011
JP 2002-165757 A 6/2002
(Continued)

OTHER PUBLICATIONS

English Abstract only of JP 2007-209770 dated Aug. 23, 2007.

*Primary Examiner* — Behrooz Senfi
(74) *Attorney, Agent, or Firm* — Scully, Scott, Murphy & Presser, P.C.

(57) ABSTRACT

An image processing apparatus is provided with: a first feature value calculating section calculating a first feature value for each of pixels constituting an image obtained by picking up an image of a subject; a region dividing section dividing the image into multiple regions on the basis of the first feature values; a second feature value calculating section calculating a second feature value for each of the divided regions; a classification section performing classification with regard to which of multiple kinds of attributes each region of the multiple regions has, on the basis of the second feature value; a judgment section judging whether a region having a predetermined attribute exists or not; and a diagnostic support information calculating section correcting an attribute value of the region having the predetermined attribute to calculate diagnostic support information for supporting a diagnosis.

7 Claims, 8 Drawing Sheets

(51) Int. Cl.
  *A61B 1/05* (2006.01)
  *A61B 1/06* (2006.01)
  *G06T 7/00* (2006.01)
  *A61B 1/04* (2006.01)

(52) U.S. Cl.
  CPC ............ *A61B 1/0669* (2013.01); *G06T 7/0012* (2013.01); *G06T 2207/10024* (2013.01); *G06T 2207/10068* (2013.01); *G06T 2207/20081* (2013.01); *G06T 2207/30096* (2013.01); *G06K 2209/053* (2013.01)
  USPC ............................................ 348/65; 600/109

(56) References Cited

U.S. PATENT DOCUMENTS

| | | | |
|---|---|---|---|
| 8,285,016 B2 * | 10/2012 | Tanaka | 382/128 |
| 2011/0069876 A1 | 3/2011 | Kanda | |
| 2012/0078043 A1 * | 3/2012 | Miyayashiki et al. | 600/109 |

FOREIGN PATENT DOCUMENTS

| | | |
|---|---|---|
| JP | 2009-291415 A | 12/2009 |
| JP | 4451460 B2 | 4/2010 |
| WO | WO 2009/148092 A1 | 12/2009 |

* cited by examiner

| REGION | ATTRIBUTE | AREA |
|---|---|---|
| Ra | A4 | 0.4 |
| Rb | A6 | 0.2 |
| Rc | A3 | 0.1 |
| Rd | A4 | 0.3 |

(B)

| VECTOR COMPONENT (ATTRIBUTE) | VECTOR COMPONENT VALUE (ATTRIBUTE VALUE) | CORRECTION VALUE |
|---|---|---|
| A1 | 0.0 | |
| A2 | 0.0 | |
| A3 | 0.1 | |
| A4 | 0.7 | |
| A5 | 0.0 | |
| A6 | 0.2 | 0.4 |

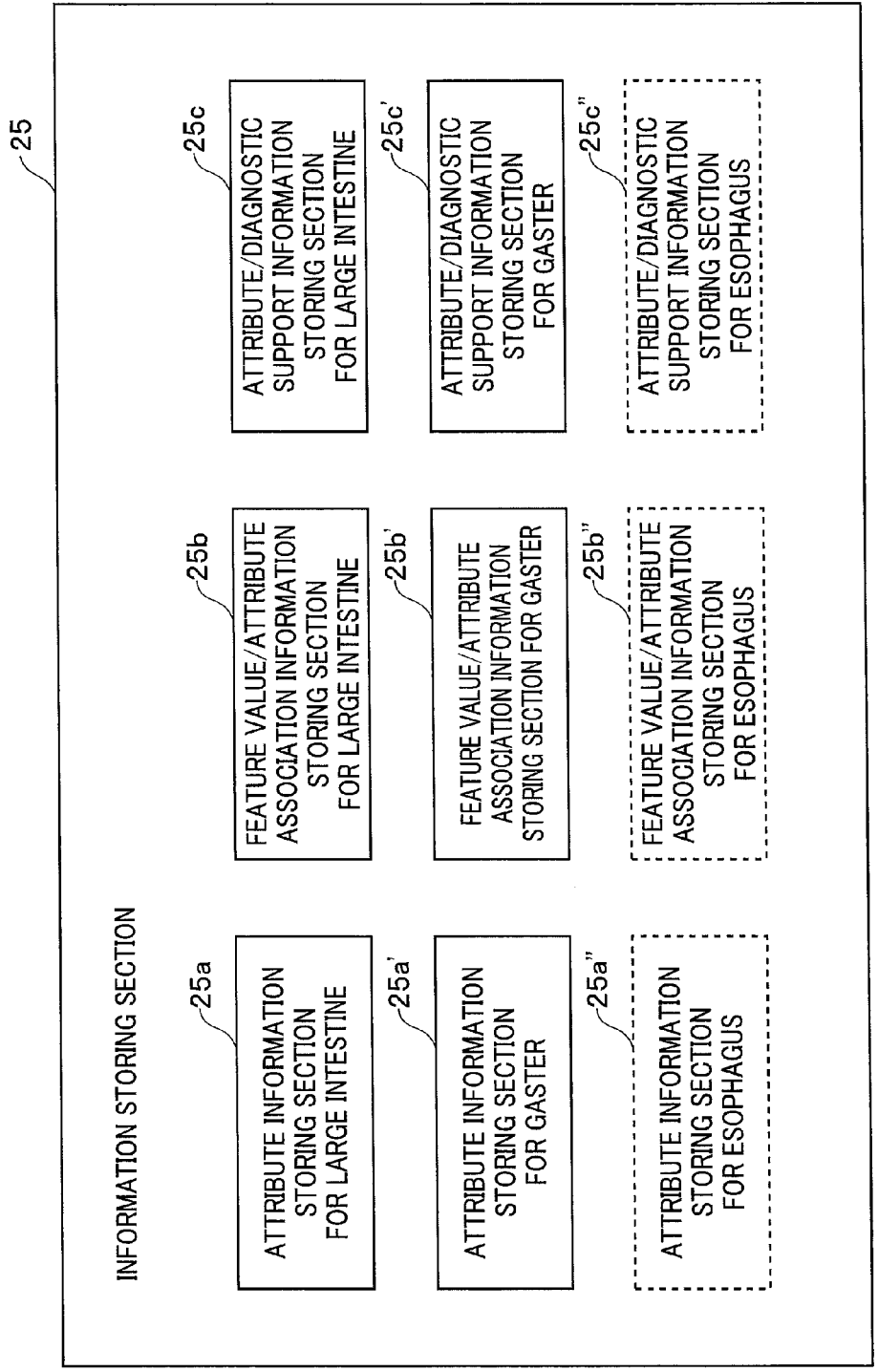

IMAGE PROCESSING APPARATUS

CROSS REFERENCE TO RELATED APPLICATION

This application is a continuation application of PCT/JP2012/080679 filed on Nov. 28, 2012 and claims benefit of Japanese Application No. 2012-064195 filed in Japan on Mar. 21, 2012, the entire contents of which are incorporated herein by this reference.

BACKGROUND OF THE INVENTION

1. Field of the Invention

The present invention relates to an image processing apparatus performing image processing for an image obtained by picking up an image of a subject.

2. Description of the Related Art

Various image processing is performed according to purposes of use for an image acquired by an image pickup apparatus for picking up an image of a subject.

In a medical field, endoscopes which are inserted into a body cavity to perform endoscopy are widely used.

An insertion section of an endoscope is inserted into a body cavity, and an image of an affected part or the like in the body cavity is picked up by an image pickup device provided at a distal end portion of the insertion section, image-processed by an image processing apparatus and displayed on a display device as an endoscopic image.

In recent years, an image processing apparatus has been proposed which calculates diagnostic support information for supporting a diagnosis by image processing, for an image or an endoscopic image acquired by the image pickup device of an endoscope, so that the surgeon can make a diagnosis more smoothly.

For example, Japanese Patent Publication No. 4451460 discloses an image processing apparatus which divides an endoscopic image obtained by picking up a living mucosa into regions according to similar tissue structures, performs, for each divided region, a discrimination/classification process on the basis of a predetermined feature value, and displays a classification result of the discrimination/classification in association with each region as diagnostic support information.

SUMMARY OF THE INVENTION

An image processing apparatus according to an aspect of the present invention is provided with: a first feature value calculating section calculating, in an arbitrary region of an image obtained by picking up an image of a subject, a first feature value for each of pixels constituting the arbitrary region; a region dividing section dividing the arbitrary region into multiple regions on the basis of the first feature values; a second feature value calculating section calculating a second feature value for each region of the multiple regions divided by the region dividing section; a classification section classifying each region of the multiple regions divided by the region dividing section into any of multiple kinds of attributes on the basis of the second feature value; a diagnostic support information calculating section calculating an attribute value based on an area or a number, for each attribute of a same kind among the multiple kinds of attributes classified by the classification section; a judgment section judging whether a region having a predetermined attribute exists or not among the multiple regions divided by the region dividing section; and a correction section correcting, when it is judged by the judgment section that the region having the predetermined attribute exists, the attribute value for the region classified into the predetermined attribute on the basis of attribute values calculated for attributes other than the predetermined attribute, wherein the diagnostic support information calculating section calculates diagnostic support information for supporting a diagnosis for the predetermined region on the basis of the attribute value corrected by the correction section for the region having the predetermined attribute and the attribute values calculated by the diagnostic support information calculation section for the multiple regions other than the region having the predetermined attribute.

An image processing apparatus according to another aspect of the present invention is provided with: a first feature value calculating section calculating, in an arbitrary region of an image obtained by picking up an image of a subject, a first feature value for each of pixels constituting the arbitrary region; a region dividing section dividing the arbitrary region into multiple regions on the basis of the first feature values; a second feature value calculating section calculating a second feature value for each of the regions divided by the region dividing section; an attribute information storing section storing in advance each of pieces of attribute information about an attribute to be an indicator of a lesion with a high degree of malignancy, an attribute to be an indicator of a lesion with a low degree of malignancy and an attribute for which a benignancy/malignancy judgment is difficult to make; a classification section classifying each of the regions divided by the region dividing section into any of the respective pieces of attribute information stored in the attribute information storing section on the basis of the second feature value calculated by the second feature value calculating section; and a diagnostic support information calculating section calculating, for the arbitrary region, diagnostic support information for supporting a diagnosis, on the basis of rates of attributes which two or more regions among the multiple regions classified by the classification section have.

BRIEF DESCRIPTION OF THE DRAWINGS

FIG. 3 is a diagram schematically showing an image inputted from an image inputting section, an image divided into regions and the like;

FIG. 8 is a diagram showing component values or the like of a multidimensional vector in FIG. 7; and FIG. 9 is a diagram showing information storage contents of an information storing section in a second embodiment of the present invention.

DETAILED DESCRIPTION OF THE PREFERRED EMBODIMENTS

Embodiments of the present invention will be described below with reference to drawings.

First Embodiment

Figure 1:
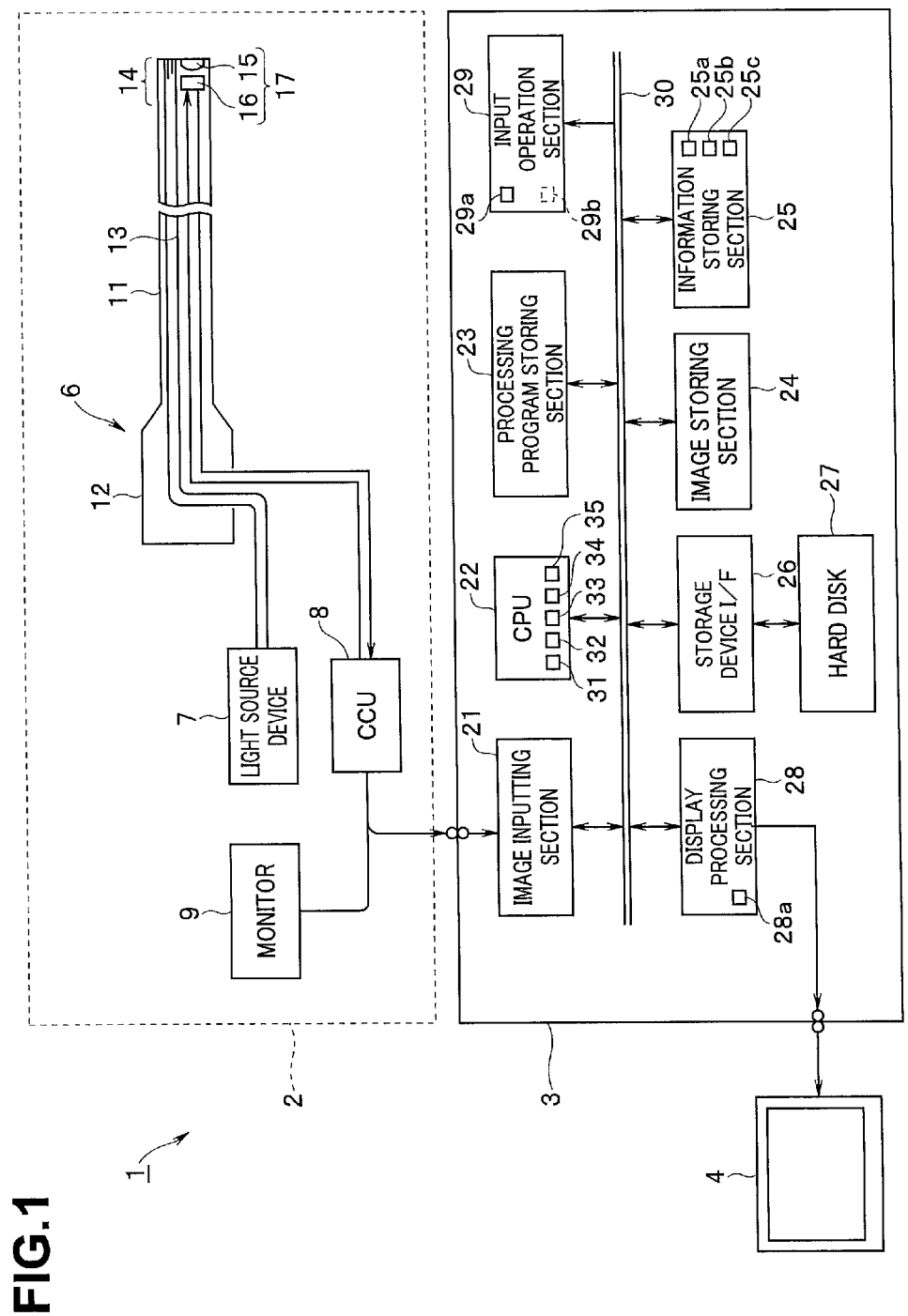
FIG. 1 is a diagram showing a whole configuration of an endoscope system provided with a first embodiment of the present invention.

An endoscope system 1 shown in FIG. 1 is configured by an endoscopic observation apparatus 2, an image processing apparatus 3 of the present embodiment configured by a personal computer or the like, which performs image processing for an endoscopic image as a medical image obtained by the endoscopic observation apparatus 2, and a display monitor 4 as a display device which displays an image which has been image-processed by the image processing apparatus 3.

The endoscopic observation apparatus 2 has an endoscope 6 to be inserted into a body cavity, a light source device 7 which supplies illuminating light to the endoscope 6, a camera control unit (abbreviated as a CCU) 8 as a signal processing device which performs signal processing for image pickup means of the endoscope 6, and a monitor 9 which displays an endoscopic image photographed by an image pickup device by a video signal outputted from the CCU 8 being inputted.

The endoscope 6 has an insertion section 11 to be inserted into a body cavity, an operation section 12 provided at a rear end of the insertion section 11. A light guide 13 for transmitting illuminating light is inserted through the insertion section 11.

A rear end of the light guide 13 is connected to the light source device 7. Illuminating light supplied from the light source device 7 is transferred by the light guide 13, and (the transmitted illuminating light is) emitted from a distal end face attached to an illuminating window provided at a distal end portion 14 of the insertion section 11 to illuminate an object such as an affected part.

An image pickup apparatus 17 is provided which is constituted by an objective lens 15 attached to an observation window adjoining to the illuminating window and, for example, a charge-coupled device (abbreviated as a CCD) 16 as a solid image pickup device arranged at an image forming position of the objective lens 15. An optical image formed on an image pickup surface of the CCD 16 is photoelectrically converted by the CCD 16.

The CCD 16 is connected to the CCU 8 via a signal line. By a CCD drive signal being applied from the CCU 8, the CCD 16 outputs a photoelectrically converted image signal. The image signal is signal-processed by a video processing circuit in the CCU 8 and converted to a video signal. The video signal is outputted to the monitor 9, and an endoscopic image is displayed on a display surface of the monitor 9. The video signal is also inputted to the image processing apparatus 3.

The image processing apparatus 3 has an image inputting section 21 which inputs a video signal corresponding to an endoscopic image (hereinafter abbreviated simply as an image) inputted from the endoscopic observation apparatus 2, a CPU 22 as a central processing unit which performs image processing for image data inputted from the image inputting section 21, and a processing program storing section 23 configured by a memory or the like which stores a processing program (a control program) which causes image processing to be executed by the CPU 22.

The image processing apparatus 3 has an image storing section 24 configured by a memory or the like which stores image data and the like inputted from the image inputting section 21, an information storing section 25 configured by a memory or the like which stores information and the like processed by the CPU 22, a hard disk 27 as a storage device which stores image data, information and the like processed by the CPU 22 via a storage device interface 26, a display processing section 28 configured by a display processing circuit or the like which performs display processing for displaying image data and the like processed by the CPU 22, and an input operation section 29 configured by a keyboard and the like for a user to input data such as parameters and the like for image processing or perform an instruction operation.

A video signal generated by the display processing section 28 is displayed on the display monitor 4 as image display means, and a processed image which has been image-processed is displayed on a display surface of the display monitor 4.

Note that the image inputting section 21, the CPU 22, the processing program storing section 23, the image storing section 24, the information storing section 25, the storage device interface 26, the display processing section 28 and the input operation section 29 are connected to one another via a data bus 30.

Figure 2:
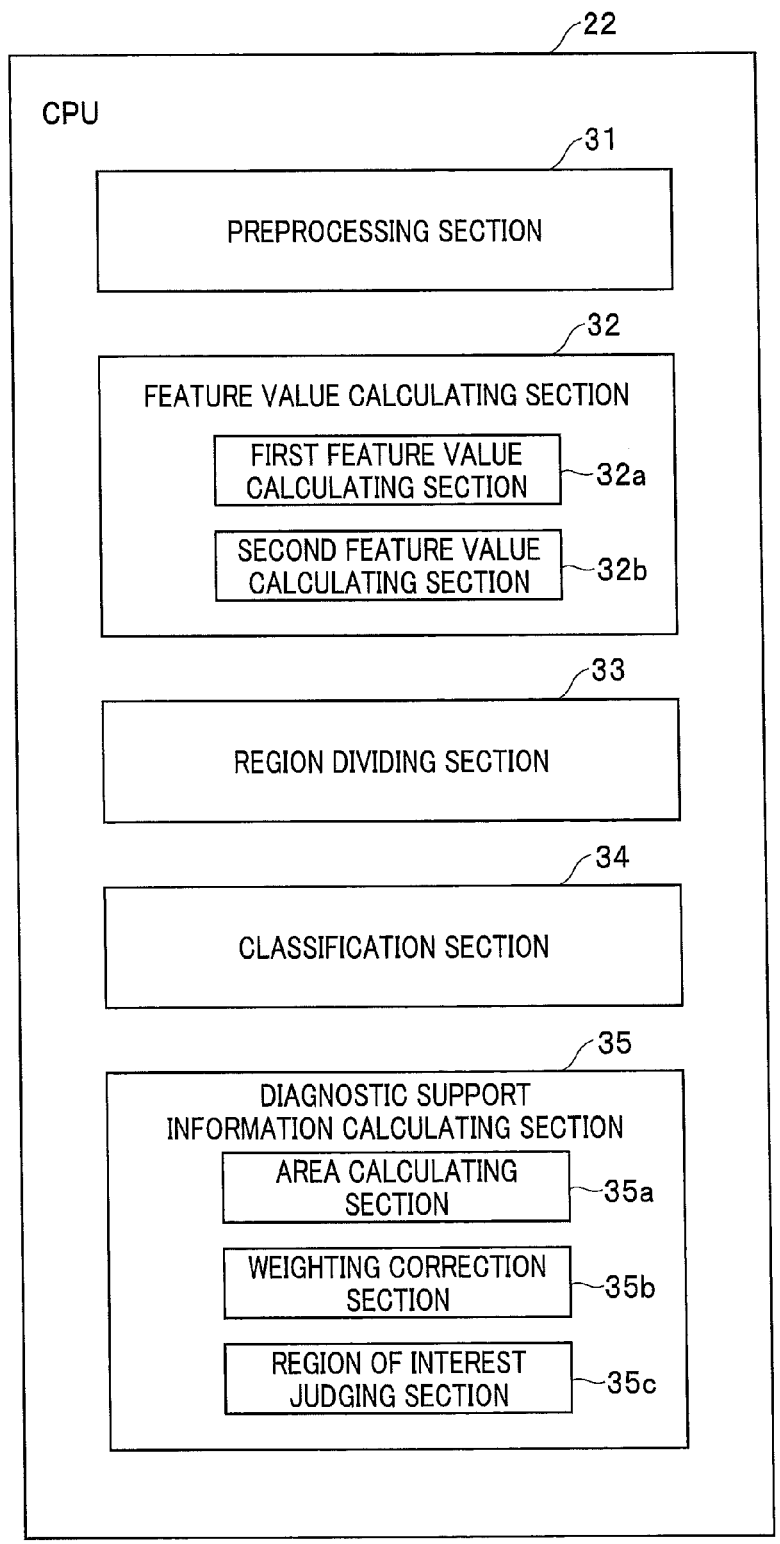
FIG. 2 is a block diagram showing main processing functions configured by a CPU constituting an image processing apparatus in FIG. 1.

FIG. 2 shows main processing functions configured by the CPU 22 in the present embodiment. As shown in FIG. 2, the CPU 22 has a processing function of a preprocessing section 31 which performs preprocessing such as noise suppression and reverse γ correction for an image inputted from the image inputting section 21.

Note that FIG. 3(A) schematically shows an image inputted from the image inputting section 21 to the image processing apparatus 3.

The CPU 22 is also provided with a processing function of a feature value calculating section 32 including a first feature value calculating section 32a which calculates a first feature value for each of pixels in an image processed by the preprocessing section 31, and a processing function of a region dividing section 33 which divides the image into multiple regions on the basis of the first feature values.

The first feature value calculating section 32a calculates each of signal values of R, G and B signals as color signals forming an image, a value calculated by operation of each signal value such as G/R and G/(R+G+B), a luminance value of a luminance signal, a texture feature (a feature of texture) an image has, a filter output value(s) of multiple frequency components or a particular frequency component with the use of a frequency band filter for separating a frequency, and the like as the first feature values.

The region dividing section 33 performs division into multiple regions on the basis of the first feature values using a well-known clustering technique or the like. The clustering technique may be non-hierarchical clustering such as k-mean clustering (a k-means method) or may be hierarchical clustering such as a nearest neighbor method. Other region dividing methods may be used. FIG. 3(B) shows multiple regions Ra to Rd divided by the region dividing section 33.

The feature value calculating section 32 has a second feature value calculating section 32b which calculates a second feature value for each region Ri (i=a to d) of the multiple regions Ra to Rd divided by the region dividing section 33.

For example, the second feature value calculating section 32b may calculate a feature value similar to the first feature value by the first feature value calculating section 32a for each region Ri as the second feature value. However, for each region, statistics such as an average value or an amount of variance of the various feature values such as each of the signal values of the R, G and B signals, the luminance value, the texture feature and the filter output value described above are also calculated as the second feature values.

The CPU 22 also has a processing function of a classification section 34 which performs classification with regard to which of multiple kinds of attributes prepared in advance each region Ri of the multiple regions Ra to Rd divided by the region dividing section 33 has.

Therefore, for example, the information storing section 25 shown in FIG. 1 has an attribute information storing section 25a which stores information about the multiple kinds of attributes prepared in advance.

The classification section 34 performs the classification with regard to which of the multiple kinds of attributes stored in the attribute information storing section 25a each region has. When the classification section 34 classifies multiple regions, for example, M regions into (regions of) attributes the respective regions have, such classification is performed that regions of a predetermined number of attributes equal to or smaller than M is obtained after the classification since there is a possibility that regions having the same attribute exist.

The above attribute information storing section 25a stores attributes shown below in advance to cope with a case of making a diagnosis, for example, for living mucous tissue of a large intestine as an examination-target living tissue (living mucous tissue).

A1. Regular vessels region (blood vessel region) (+)
A2. Regular surface pattern region (surface pattern region) (+)
A3. Irregular vessels region (−)
A4. Irregular surface pattern region (−)
A5. Extreme color-tone change region (−)
A6. Anhistic region (±)
A7. Bleeding region (—)

The above attributes of A1 to A7 are set in advance for the case of an examination-target living mucous tissue of a large intestine for the purpose of calculating diagnostic support information which is to be an estimate or indicator of its lesion. When attempting to classify image data of the living mucous tissue of the large intestine collected in the past according to multiple attributes, the image data can be classified according to the above attributes of A1 to A7.

The sign (+) attached after the attribute indicates an attribute to be an indicator of a lesion with a low degree of malignancy (a low possibility of a lesion), and the sign (−) indicates an attribute to be an indicator of a lesion with a high degree of malignancy (a high possibility of a lesion).

The sign (±) after the attribute of A6 indicates an attribute (a predetermined attribute) to be an indicator indicating that it is difficult to judge whether the degree of malignancy is high or low because there is not a structure (that is, a structure is not shown substantially). The predetermined attribute which an anhistic region as a region of interest has is such an attribute that it is difficult to judge only by the region having the predetermined attribute whether the region is a region corresponding to the AVA described above or, rather than AVA, a region where blood vessels are merely invisible.

Therefore, for the region having the attribute of the anhistic region (±) (that is, the region of interest), the present embodiment corrects an attribute value as the value of the attribute on the basis of a rate of an area of each of attributes which a single or multiple surrounding regions adjoining to the region have (area rates of attributes of multiple regions), (and calculates diagnostic support information using the corrected attribute value) as described later.

Note that diagnostic support information such as a corresponding lesion name or symptom name is calculated according to attribute values or rates of the multiple kinds of attributes (in other words, a discrimination space as a virtual space of multiple kinds of numbers of dimensions) as described later. The sign (—) after the attribute of A7 indicates a particular attribute with a high degree of malignancy (a very high possibility of a lesion).

If a region having the particular attribute is detected, diagnostic support information about a corresponding lesion name is calculated irrespective of other attributes or attribute values. That is, the attribute of A7 is significantly different from the cases of the attributes of A1 to A6 (at least a case of calculating corresponding diagnostic support information on the basis of calculation of each attribute value). Therefore, description below is mainly related to the attributes of A1 to A6.

As described above, in the present embodiment, the attribute information storing section 25a mainly stores information about first attributes (specifically, A1 and A2) to be an indicator of a lesion with a low degree of malignancy, second attributes (specifically, A3 to A5) to be an indicator of a lesion with a high degree of malignancy, and a third attribute (specifically, A6) as the predetermined attribute for which it is difficult to judge the degree of malignancy, for the multiple regions Ra to Rd in advance.

Figure 4:
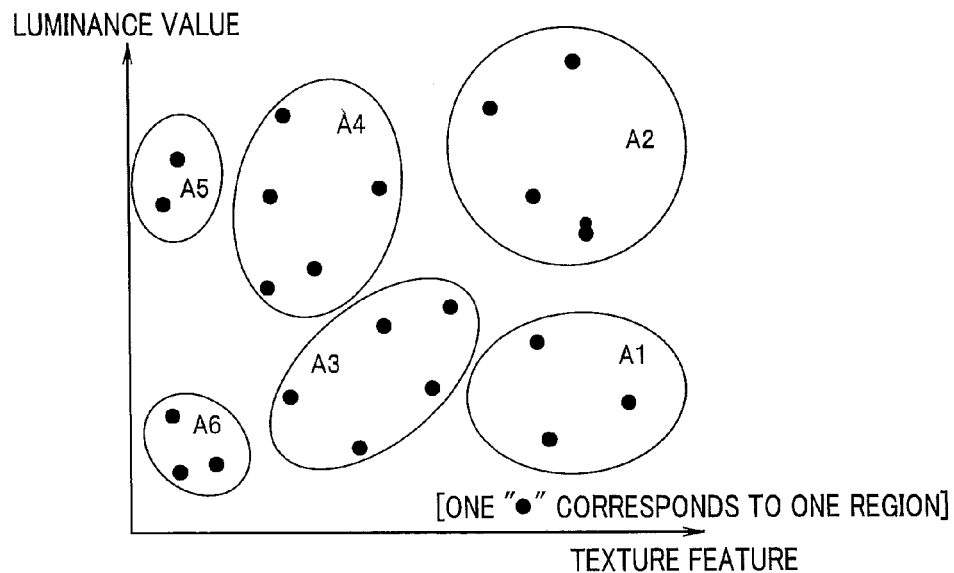
FIG. 4 is a diagram showing second feature values and a concept of a feature value/attribute discrimination space in which multiple kinds of attributes exist in each of particular ranges of the second feature values.

The classification section 34 also calculates classification (discrimination) boundaries about the multiple kinds of attributes A1 to A6 described above using the second feature values in a well-known discrimination/classification technique (Fisher's linear discriminant function, Support Vector Machine or the like), with the use of supervised data (training data) prepared in advance. FIG. 4 schematically shows a discrimination space for discriminating (classifying) attributes calculated in advance with the use of the well-known discrimination/classification technique.

The example in FIG. 4 shows a conceptual diagram of a discrimination space in which, for example, a luminance value and a texture feature as the second feature values are set as orthogonally intersecting coordinate axes, and ranges in which the six attributes A1 to A6 discriminably exist are calculated according to a luminance value and a texture feature a region Ri has. FIG. 4 shows a case of a two-dimensional space with two second feature values. In the case of three second feature values, the space is a three-dimensional space, and, in the case of one second feature value, the space is one-dimensional (space). In FIG. 4, one black point (small circle) corresponds to one region.

For example, the information storing section 25 has a feature value/attribute association information storing section 25b storing (second) feature value/attribute association information (or information for attribute classification) in which values of second feature values and ranges in which respective corresponding attributes exist are associated.

The classification section 34 can easily classify (identify) an attribute corresponding to second feature values such as a luminance value and a texture feature calculated for each region Ri by referring to the feature value/attribute association information.

FIG. 3(C) shows that the classification section 34 has performed attribute classification referring to the feature value/attribute association information for the regions Ra to Rd in FIG. 3(B).

On an image for which attribute classification has been performed, a user such as a surgeon can set a range Ro of a region about which diagnostic support information is to be obtained from the image processing apparatus 3 (hereinafter, a region of concern). The user such as a surgeon sets the range Ro of the region of concern about which diagnostic support information is to be obtained, for the image for which attribute classification has been performed, from the input operation section 29 in FIG. 1. The input operation section 29 forms a range setting section 29a for the user to set the region-of-concern range Ro.

By an input operation of setting the region-of-concern range Ro, the CPU 22 sets the region-of-concern range Ro on the image for which attribute classification has been performed.

FIG. 3(D) shows that the region-of-concern range Ro has been set on the image for which attribute classification has been performed. Note that setting of the region-of-concern range Ro is not limited to the case of performing the setting for an image for which attribute classification has been performed but can be performed for an image before attribute classification being performed.

As shown in FIG. 2, the CPU 22 has a processing function of a diagnostic support information calculating section 35 which calculates diagnostic support information for supporting a diagnosis by the surgeon, on the basis of attribute information about each of a predetermined number of regions Ri classified by the classification section 34, more specifically, on the basis of information about multiple kinds of attributes with regard to which attribute each region Ri has and area information about regions having the respective attributes.

The diagnostic support information calculating section 35 calculates a lesion name, symptom name or the like prepared in advance for examination-target living tissue as the diagnostic support information. In the present embodiment, three lesion names shown below are prepared as diagnostic support information in the case of performing examination of a large intestine.

D1. Hyperplastic polyp
D2. Adenoma
D3. Cancer

In the present embodiment, similarly to making it possible to classify (identify) an attribute corresponding to a second feature value from the second feature value (which the region Ri has) described above, boundaries discriminating multiple pieces of diagnostic support information (specifically, D1 to D3) are calculated with the use of supervised data in advance and with the use of multiple kinds of attributes (specifically, the attributes of A1 to A6) by a well-known discrimination/classification technique.

Figure 5:
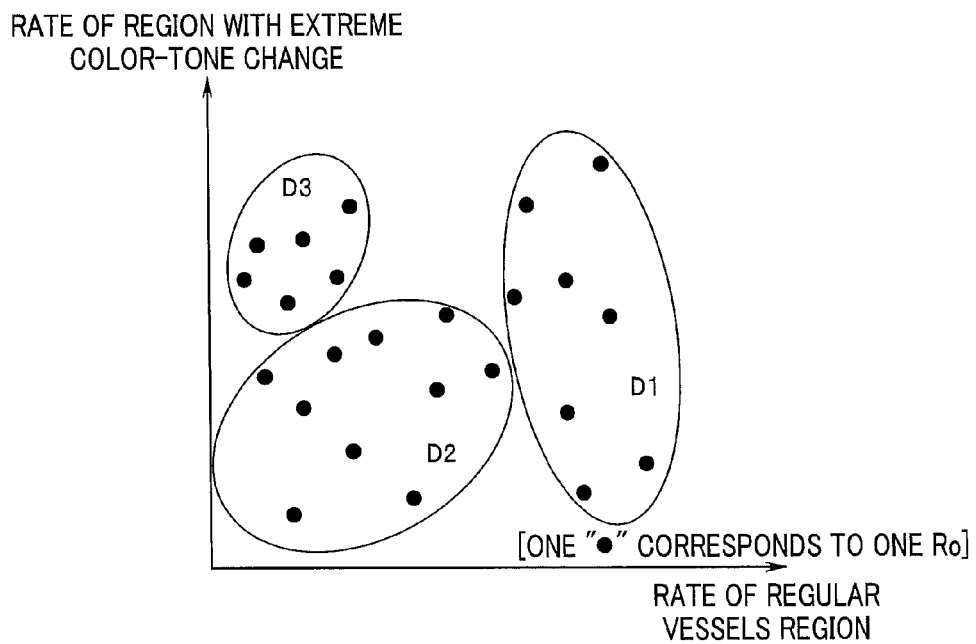
FIG. 5 is a diagram showing multiple kinds of attributes and a concept of an attribute/diagnostic support information discrimination space in which different diagnostic support information exists in each of particular ranges of the multiple kinds of attributes.

FIG. 5 shows a conceptual diagram of attribute/diagnostic support information association information calculated in advance with the use of supervised data in a two-dimensional vector space (a discrimination space) in which a regular vessels region and a region with extreme color-tone change are set as orthogonally intersecting coordinate axes.

FIG. 5 schematically shows ranges in which multiple diagnostic support information (specifically, D1 to D3) discriminably exist in a simplified two-dimensional space. Actually, ranges in which multiple pieces of diagnostic support information different from one another discriminably exist are determined in a six-dimensional vector space (a discrimination space) in which each of the attributes of A1 to A6 is regarded as a different vector component. Note that one black point (small circle) corresponds to one range Ro in FIG. 5.

The information storing section 25 has an attribute/diagnostic support information association information storing section 25c which stores the attribute/diagnostic support information association information calculated in advance with the use of supervised data.

The attribute/diagnostic support information association information storing section 25c as information storing means associates an attribute value calculated, for each attribute, in a multidimensional vector space with multiple kinds of attributes as vector components, respectively, by a sum total of areas of regions having each attribute with a component value of each vector, and stores information about ranges in the vector space in which multiple pieces of diagnostic support information different from one another according to the component values of the multidimensional vector. Note that the attribute/diagnostic support information association information storing section 25c forms a diagnostic support information storing section storing diagnostic support information which is used to calculate diagnostic support information on the basis of information about area rates of attributes which a predetermined number of regions classified by the classification section 34 have, respectively, or the number of regions having each of the attributes.

From information about an attribute each region Ri classified by the classification section 34 has and information about the area of each region Ri, the diagnostic support information calculating section 35 calculates diagnostic support information by referring to the attribute/diagnostic support information association information stored in the attribute/diagnostic support information association information storing section 25c.

For this purpose, the diagnostic support information calculating section 35 has an area calculating section 35a which calculates the area each region Ri has. The diagnostic support information calculating section 35 determines a value of each attribute among multiple kinds of attributes (specifically, A1 to A6) by associating the value with a value of the areas of regions having the attribute. In other words, a value (a vector component) of the coordinate axis of each attribute in the attribute diagnostic support information association discrimination space (the multidimensional vector space of attributes) shown in FIG. 5 corresponds to a value (a rate) of the area of a single or multiple regions having the attribute.

Therefore, the diagnostic support information calculating section 35 can easily calculate, on the basis of a value of each attribute which is a result of calculating, for each of multiple kinds of attributes, the area of a single or multiple regions having each attribute, diagnostic support information corresponding to the value of each of the attributes from the attribute/diagnostic support information association information.

On the other hand, in the case of such a classification result that a region Ri having a predetermined (kind of) attribute, specifically, the attribute of A6 is included (in a region-of-concern range Ro for which the surgeon desires diagnostic support), information about the region Ri to be a region of interest having the attribute of A6 cannot be effectively used for diagnostic support information. That is, since the attribute of A6 is such that it is difficult to make a discrimination between the first attribute which acts with a tendency of reducing the degree of malignancy of a lesion and the second attribute which acts with a tendency of increasing the degree of malignancy of a lesion, the attribute of A6 cannot be effectively used for calculation of diagnostic support information in the state of the attribute and the region being as they are.

Therefore, if having performed classification in the state of the predetermined attribute as the attribute of A6 being included within the region-of-concern range Ro, the diagnostic support information calculating section 35 of the present embodiment performs a process of making a correction to an attribute value close to any of the first attribute or the second attribute, on the basis of attributes which multiple regions existing around a region of interest having the predetermined attribute and the areas of the regions, with the region of interest as the center.

That is, the diagnostic support information calculating section 35 shown in FIG. 2 has a weighting correction section 35b which, for a region to be a region of interest having a particular attribute, corrects a value of the attribute, for example, by weighting. For a region having the attribute of A6, the diagnostic support information calculating section 35 calculates a value of the attribute weighting-corrected by the weighting correction section 35b and, further calculates, on the basis of values of the attributes of A1 to A5, respectively, calculated on the basis of the attributes and areas of regions having the respective attributes, diagnostic support information corresponding to the value of each attribute from the attribute/diagnostic support information association information. Note that the diagnostic support information calculating section 35 has a region of interest judging section 35c as region of interest judging means for judging whether a region which includes a predetermined attribute like the attribute A6 described above (referred to as a region of interest) is included in the region-of-concern range Ro (see FIG. 2).

(The diagnostic support information calculating section 35 of) the CPU 22 sends the calculated diagnostic support information to the display processing section 28 in FIG. 1, and the display processing section 28 displays the calculated diagnostic support information on the display monitor 4. The display processing section 28 forms a diagnostic support information display processing section 28a which performs a process of displaying the diagnostic support information, and the display monitor 4 forms a diagnostic support information displaying section which displays the diagnostic support information.

Note that, though FIG. 2 shows a case where the preprocessing section 31, the feature value calculating section 32, the region dividing section 33, the classification section 34 and the diagnostic support information calculating section 35 are configured by the CPU 22, the sections are not limited to the case of being configured by the CPU 22 but may be configured with hardware such as a dedicated electronic circuit.

The image processing apparatus 3 of the present embodiment configured as described above is characterized in being provided with: the first feature value calculating section 32a as first feature value calculating means for, from an image obtained by picking up an image of a subject, calculating a first feature value for each of pixels constituting the image; the region dividing section 33 as region dividing means for dividing the image into multiple regions on the basis of the first feature values; the second feature value calculating section 32b as second feature value calculating means for calculating a second feature value for each of the regions divided by the region dividing means; the classification section 34 as classification means for performing classification with regard to which of multiple kinds of attributes each region of the multiple regions has, on the basis of the second feature values; and the diagnostic support information calculating section 35 as diagnostic support information calculating means for calculating diagnostic support information for supporting a diagnosis, on the basis of rates of attributes which a predetermined number of (two or more) regions among the multiple regions classified by the classification means have.

Next, a process of calculating the diagnostic support information by the image processing apparatus 3 of the present embodiment will be described with reference to FIG. 6.

In a state that the endoscopic observation apparatus 2, the image processing apparatus 3 and the display monitor 4 are connected as shown in FIG. 1, the surgeon powers on the endoscope system 1.

In order to examine, for example, the large intestine of a patient as a subject, the surgeon inserts the endoscope 6 into the large intestine.

An image picked up by the image pickup apparatus 17 of the endoscope 6 is displayed on the monitor 9 as well as being inputted to the image processing apparatus 3 through the image inputting section 21.

Figure 6:
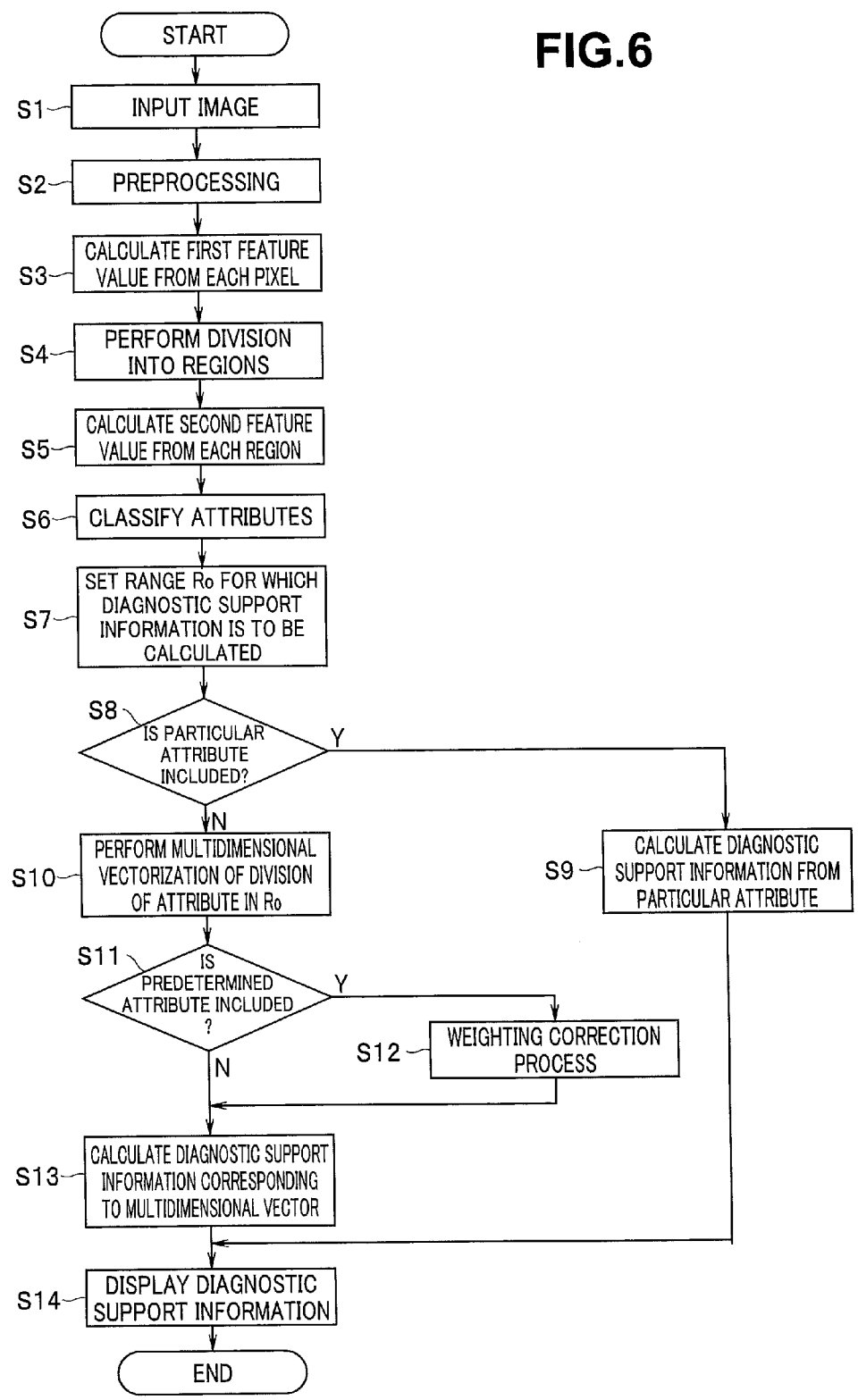
FIG. 6 is a flowchart showing a processing procedure for calculating the diagnostic support information in the first embodiment.

That is, as shown in step S1 in FIG. 6, for example, an analog image is A/D converted to a digital image and inputted to the image processing apparatus 3 by the image inputting section 21. The image is temporarily stored, for example, in the image storing section 24. FIG. 3(A) schematically shows the image. Note that, though a treatment target image I is set in a region in an almost oval shape in a central part in FIG. 3(A), the setting is not limited to the case of such a region.

As shown in S2, (the preprocessing section 31 of) the CPU 22 performs preprocessing such as noise suppression and reverse γ correction for the treatment target image I.

As shown in step S3, (the first feature value calculating section 32a of) the CPU 22 calculates, from each pixel of the image I processed by the preprocessing section 31, first feature values such as R, G and B signal values, a value calculated by operation of each signal value, a luminance value, a texture feature and a filter output value.

As shown in step S4, (the region dividing section 33 of) the CPU 22 performs division into multiple regions on the basis of the first feature values using the k-means method, the nearest neighbor method or the like as a well-known clustering technique.

FIG. 3(B) shows multiple regions Ra to Rd divided by the region dividing section 33.

As shown in step S5, (the second feature value calculating section 32b of) the CPU 22 calculates second feature values for each region Ri among the multiple divided regions Ra to Rd. For each region Ri, the second feature value calculating section 32b calculates statistics, such as an average value or an amount of variance of each of the signal values of the R, G and B signals, the value calculated by operation of each signal value, the luminance value, the texture feature and the like described above, as the second feature values. Note that a feature value of a kind different from the first feature values and the statistic thereof may be used.

As shown in next step S6, (the classification section 34 of) the CPU 22 performs classification with regard to which attribute among multiple kinds of attributes stored in the attribute information storing section 25a each region Ri among the multiple regions Ra to Rd divided by the region dividing section 33 has, on the basis of the second feature values calculated by the second feature value calculating section 32b.

In this case, if the feature value/attribute association information described with reference to FIG. 4 is stored in the feature value/attribute association information storing section 25b in advance, an attribute corresponding to each region Ri can be easily identified (classified).

FIG. 3(D) shows that each the multiple regions Ra to Rd is classified into a corresponding attribute by step S6. Specifically, the classification section 34 classifies the region Ra to have the attribute of A4, the region Rb to have the attribute of A6, the region Rc to have the attribute of A3 and the region Rd t to have the attribute of A4.

As shown in next step S7, by an input operation of setting a region-of-concern range Ro for which diagnostic support information is to be calculated by the surgeon from the input operation section 29, the CPU 22 sets the region-of-concern range Ro on the image I for which attribute classification has been performed.

Figure 3:
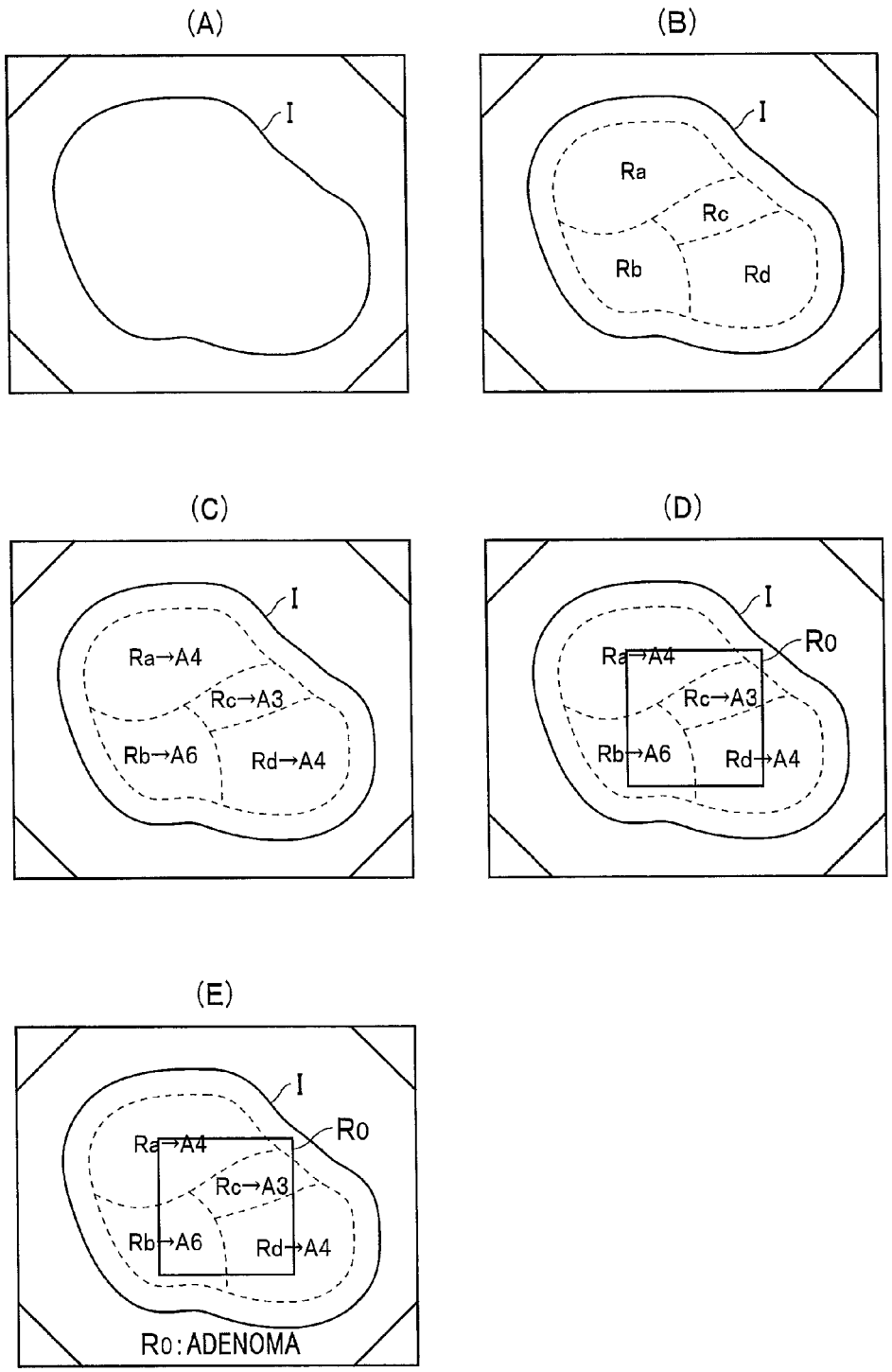

FIG. 3(D) shows that the above range Ro has been set on the image for which attribute classification has been performed. Note that, as described above, the process shown in step S7 may be performed on the image I before attribute classification being performed. Though the range Ro is set as one rectangular region in FIG. 3, the shape and size of the range Ro and the number of the ranges Ro are not limited. It is also possible to, without especially setting the range Ro, set the whole image I as a region of concern (this is equal to setting the whole image I as the range Ro).

In next step S8, (the diagnostic support information calculating section 35 of) the CPU 22 judges whether or not the range Ro set at step S7 includes a region having an attribute like A7, that is, a particular attribute having a high possibility of corresponding to a particular lesion and being such an attribute that an indicator of degree of malignancy is remarkable.

If judging that the range Ro includes the region having the particular attribute, (the diagnostic support information calculating section 35 of) the CPU 22 calculates corresponding diagnostic support information from the particular attribute irrespective of other attributes at step S9. If a region having a particular attribute like A7 exists, (the diagnostic support information calculating section 35 of) the CPU 22 calculates diagnostic support information about a lesion name of cancer and proceeds to a process of step S14.

On the other hand, if judging that the range Ro does not include the region having the particular attribute, (the diagnostic support information calculating section 35 of) the CPU 22 starts a process of performing multidimensional vectorization of rates of the multiple kinds of attributes in the range Ro with multiple kinds of numbers of dimensions (abbreviated as multidimensional vectorization of attributes) at next step S10. Note that contents of the process of the multidimensional vectorization of attributes will be described later with reference to FIG. 7.

When the process of multidimensional vectorization starts, (the region of interest judging section 35c of the diagnostic support information calculating section 35 of) the CPU 22 judges whether or not the range Ro includes a region having a predetermined attribute like A6 (in other words, a region of interest having such a predetermined attribute that it is difficult to calculate appropriate diagnostic support information only on the basis of the region) at next step S11 in FIG. 6.

As shown in FIG. 3(D), in the case of a judgment result that the range Ro includes a region of interest having a predetermined attribute, (the weighting correction section 35b of) the diagnostic support information calculating section 35 corrects a value of the attribute, that is, an attribute value by a weighting correction process for the region of interest having a predetermined attribute at step S12 and, after that, proceeds to a process of next step S13.

On the other hand, if judging that the range Ro does not include the region having a predetermined attribute, (the weighting correction section 35b of) the diagnostic support information calculating section 35 proceeds to a process of step S13.

At step S13, (the diagnostic support information calculating section 35 of) the CPU 22 calculates corresponding diagnostic support information from information about the attribute values of the multiple kinds of attributes which have been multidimensionally vectorized and sends the calculated diagnostic support information to the display processing section 28.

At next step S14, (the diagnostic support information display processing section 28a of) the display processing section 28 performs a process of displaying the diagnostic support information and displays the diagnostic support information on a display screen of the display monitor 4. FIG. 3(E) shows that the calculated diagnostic support information (specifically, a lesion name of an adenoma) is displayed for the range Ro. Note that the diagnostic support information may be displayed on the range Ro.

By referring to the diagnostic support information displayed in this way, the surgeon can efficiently perform endoscopy.

Next, processes by the diagnostic support information calculating section 35, such as the process of multidimensional vectorization of attributes at step S10 in FIG. 6, the weighting correction process related thereto and the like will be described with reference to FIG. 7.

Figure 7:
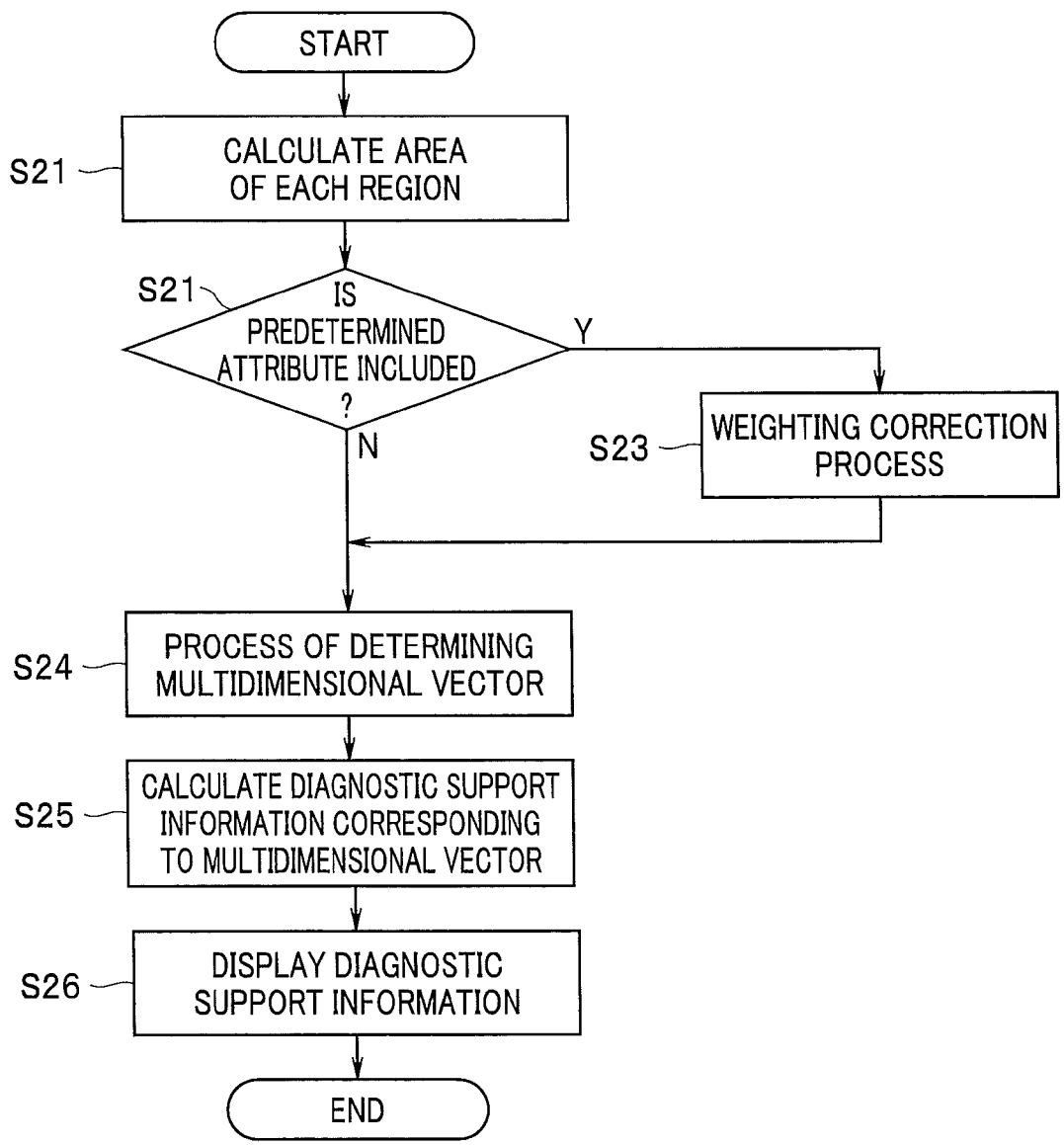
FIG. 7 is a flowchart showing a processing procedure for performing multidimensional vectorization of attributes in FIG. 6.

When the process of multidimensional vectorization of attributes starts, (the area calculating section 35a of) the diagnostic support information calculating section 35 calculates the number of pixels of or an area rate of each region included in the range Ro (in other words, area rates of attributes of the regions included in the range Ro) as shown in step S21 in FIG. 7.

FIG. 8(A) shows respective area rates of the regions Ra to Rd calculated by the area calculating section 35a. Note that the attribute of each region Ri is also shown in FIG. 8(A).

At step S22, (the diagnostic support information calculating section 35 of) the CPU 22 judges whether or not the range Ro includes a region of interest having a predetermined attribute, similarly to step S9. If the region of interest having a predetermined attribute is included, (the weighting correction section 35b of) the diagnostic support information calculating section 35 performs the weighting correction process for the predetermined attribute or the region of interest including the predetermined attribute at step S23 similarly to step S10 and, after that, proceeds to a process of step S24.

On the other hand, if judging that the range Ro does not include the region of interest having a predetermined attribute, (the diagnostic support information calculating section 35 of) the CPU 22 performs a process of determining a multidimensional vector (in the specific example, a six dimensional vector) of attributes at step S24.

Since the area rates of the regions are calculated as shown in FIG. 8(A), (the diagnostic support information calculating section 35 of) the CPU 22 calculates vector component values (also referred to simply as component values) with the attributes A1 to A6 as values of six vector components of the six-dimensional vector. Note that the vector component values (component values) correspond to attribute values or rates of attributes.

In the case of data in FIG. 8(A), each of component values of A1, A2 and A5 is 0, and component values of A3, A4 and A6 are 0.1, 0.7 and 0.2, respectively. Therefore, the six-dimensional vector is calculated (determined) as in FIG. 8(B).

If the component value of A6 is 0, the flow proceeds to a process of calculating diagnostic support information (corresponding to the multidimensional vector) at step S25 in FIG. 7 (step S13 in FIG. 6). On the other hand, if the component value of A6 is not 0, the component value of A6 is corrected by the weighting correction process of step S23 to determine the six-dimensional vector. If the component value of A6 is not 0, the component value of A6 is corrected by calculating a weight correction value Wc as described below and multiplying the component value of A6 by the weight correction value Wc. The correction is performed for the attribute of A6, and correction of the other attributes of A1 to A5 is not performed.

When the range Ro is set as shown in FIG. 3(D), the regions Ra, Rc and Rd exist around the region of interest Rb having the attribute of A6 as a predetermined attribute.

Therefore, in the present embodiment, the weighting correction section 35b calculates the weight correction value Wc (for correcting the component value of A6) by a weighting correction equation (1) using a weight coefficient W shown below, the weight correction value Wc being to be a component value according to a ratio of an area rate (or the number of pixels) Ar1 of first attributes (in the specific example, A1 and A2) classified to be with a low degree of malignancy of a lesion in the regions Ra, Rc and Rd around the region of interest Rb having the predetermined attribute and an area rate (or the number of pixels) Ar2 of second attributes (in the specific example, A3 to A5) classified to be with a high degree of malignancy of a lesion in the regions Ra, Rc and Rd, at step S12 in FIG. 6 or step S23 in FIG. 7.

$$Wc=Ar2\times W/(Ar1+Ar2) \quad (1)$$

In the present embodiment, the weight coefficient W is set to 2 (W=2).

When this is applied to the specific example in FIG. 8, the correction equation (1) becomes:

$$Wc=(0.1+0.7+0.0)\times 2/(0.0+0.0+0.1+0.7+0.0)=2.0 \quad (2)$$

The weighting correction section 35b sets a correction value 0.4 obtained by correcting the component value of A6, 0.2 by 0.2×Wc using the calculated weight correction value Wc (=2.0), as a correction value of the component value of A6. As described above, the weighting correction section 35b corrects the component value 0.2 of A6 before correction to 0.4 using the weight correction value Wc.

Therefore, the component values of the six-dimensional vectors A1 to A6 are determined as 0.0, 0.0, 0.1, 0.7, 0.0 and 0.4 as shown in FIG. 8(B).

Since each component value of the six-dimensional vector has been determined, (the diagnostic support information calculating section 35 of) the CPU 22 calculates diagnostic support information corresponding to the six-dimensional vector of the attributes A1 to A6 at step S25 as shown in FIG. 7.

Furthermore, at step S26, the calculated diagnostic support information is displayed on the display monitor 4, and the process in FIG. 7 or FIG. 6 ends.

Note that the surgeon can select another image stored in the image storing section 24 and cause a similar process to be executed.

According to the image processing apparatus 3 which performs such image processing, since a process of displaying diagnostic support information for a region-of-concern range Ro specified by the surgeon is performed, the surgeon can efficiently perform endoscopy.

Furthermore, according to the image processing apparatus 3 of the present embodiment, it is possible to calculate more appropriate diagnostic support information on the basis of rates of attributes in multiple regions divided on the basis of feature values, which the respective regions have (that is, a rate of each of attributes not of the individual regions but over the multiple regions).

Furthermore, according to the image processing apparatus 3 of the present embodiment, it is possible to, even in a case where an attribute value required to calculate corresponding diagnostic support information cannot be properly calculated from an individual region, calculate a relevant attribute value from the rates of attributes which two or more regions around the region have, and, therefore, it is possible calculate more appropriate diagnostic support information.

Second Embodiment

Next, a second embodiment of the present invention will be described with reference to FIG. 9.

In the first embodiment, description has been made on the case of applying the first embodiment to a large intestine as an examination-target (diagnosis-target) site or tissue. The present embodiment is an image processing apparatus adapted to be capable of performing similar image processing for a gastric mucosa and the like.

The image processing apparatus of the present invention is similar to the image processing apparatus 3 shown in FIG. 1. In the present embodiment, however, the information storing section 25 stores an attribute information storing section 25a' for gaster as well as the attribute information storing section 25a for large intestine, as shown in FIG. 9.

The information storing section 25 also stores a feature value/attribute association information storing section 25b' for gaster as well as the feature value/attribute association information storing section 25b for large intestine, and an attribute/diagnostic support information association information storing section 25c' for gaster as well as the attribute/diagnostic support information association information storing section 25c for large intestine.

By selecting large intestine or gaster as an examination target site or tissue from an examination-target site (or tissue) inputting section 29b (indicated by a broken line in FIG. 1) provided for the input operation section 29, the CPU 22 can perform image processing, referring to information for large intestine or information for gaster selected from the information storing section 25.

In the case of selecting large intestine from the input operation section 29, the operation is similar to that of the first embodiment. Therefore, a case of selecting gaster will be described.

The attribute information storing section 25a' for gaster stores four attributes A11 to A14 shown below.

A11: Regular beehive-state blood vessel region or regular circular surface pattern region (surface pattern region) (+)

A12: Regular linear blood vessel region or regular belt-shaped surface pattern region (surface pattern region) (+)

A13: Irregular meandering blood vessel region or region where surface pattern has disappeared (−)

A14: Large-diameter blood vessel (±)

The above attributes of A11 and A12 correspond to the first attribute similarly to the attributes A1 and A2 in the first embodiment; the attribute of A13 corresponds to the second attribute similarly to the attributes A3 to A5 in the first embodiment; and the attribute of A14 corresponds to the third attribute similarly to the attribute A6 in the first embodiment. In this case, similarly to the case of A6 in the first embodiment, it is difficult to judge, only from an individual region, whether a large-diameter blood vessel is an abnormal blood vessel which appears in the case of cancer or collecting venules which appears on a normal fundic gland mucosa.

In the present embodiment also, the CPU 22 has processing functions similar to those in FIG. 2. The classification section 34, however, performs classification of regions divided by the region dividing section 33 with regard to which of the above attributes of A11 to A14 the regions have. Note that the first and second feature values calculated at that time may be the same feature values as those for large intestine, or feature values for gaster may be separately calculated.

In the present embodiment also, the attribute of A14 is regarded as a predetermined attribute, and as for a predetermined region having the predetermined attribute, (the weighting correction section 35b of) the diagnostic support information calculating section 35 corrects its attribute value similarly to the first embodiment by performing a similar weighting correction process.

As diagnostic support information for gaster, the following D11 to D14 are prepared:

D11. Normal fundic gland mucosa
D12. Normal pyloric gland mucosa
D13. Gastritis
D14. Cancer Diagnostic support information is calculated, for example, by the processing procedure in FIG. 6 in the first embodiment and displayed on the display monitor 4.

Thus, the present embodiment has advantages almost similar to those of the first embodiment.

According to the present embodiment, not only the advantages similar to those of the first embodiment are obtained but also it is possible to, by a surgeon specifying or selecting a site to be examined, calculate and display appropriate diagnostic support information for an image of the specified or selected site.

Note that an attribute information storing section 25a" for esophagus, a feature value/attribute association information storing section 25b" for esophagus and an attribute/diagnostic support information association information storing section 25c" for esophagus may be provided for the information storing section 25 as indicated by a broken line in FIG. 9 so that appropriate diagnostic support information can be provided in the case of examining an esophagus also.

In the present embodiment, a method of referring to suitable information from the information storing section 25 by selecting an examination-target site or tissue in advance has been shown as an example. However, an examination-target site or tissue may be presumed with the use of calculated various feature values.

Note that, in the embodiments described above, description has been made on an example of, in the case of performing weighting correction when a region of interest having the third attribute exists as a predetermined attribute, calculating corresponding diagnostic support information by correcting the attribute value of the attribute to a value of a sum total of regions having the same attribute that is other than the third attribute, among multiple regions around the region of interest. However, the correction may be made by regarding the number of regions having the same attribute as the attribute value of the attribute.

That is, if such classification is performed by the classification section 34 that a predetermined region having the third attribute exists, the weighting correction section 35b may correct the attribute to an attribute value weighted according to the ratio of the area of or the number of regions having a first attribute different from the third attribute around the predetermined region and the area of or the number of regions having a second attribute.

The attributes, feature values and diagnostic support information included in the information storing section 25 are not limited to those shown in the embodiments, and various modifications are possible. Note that, when the region of interest judging section 35c as region of interest judging means or region of interest selecting means described above judges or selects a region of interest from multiple regions in the range Ro, the judgment or selection may be performed as described below. Predetermined attribute specifying means for specifying a predetermined attribute, such as A6, corresponding to a region of interest from the input operation section 29 or the like may be provided to judge or select the region of interest corresponding to the predetermined attribute from the multiple regions on the basis of a predetermined attribute specified by the predetermined attribute setting means.

In the above description, a configuration has been mainly described which is provided with the range setting section 29a which sets a region-of-concern range Ro for which the diagnostic support information is to be calculated, for a single or multiple regions divided by the region dividing section 33. However, the region-of-concern range Ro may be set for the multiple regions so that the region of interest judging section 35c judges whether or not at least a part of a region of interest having a predetermined attribute is included in the multiple regions.

The embodiments described above may be partially combined.

The present invention also includes the content shown below. A diagnostic support information storing section is provided which stores a range where the diagnostic support information, including a lesion name or a symptom name prepared in advance for the subject with the use of supervised data, exists in an N-dimensional virtual space corresponding to the multiple (N) kinds of attributes. On the basis of area rates of attributes which a predetermined number of regions classified by the classification section have, respectively, or the number of regions having each of the attributes, in the multiple regions divided by the region dividing section, the diagnostic support information calculation section calculates, from a positions at which the predetermine number of regions exist in the virtual space, the diagnostic support information corresponding to the positions.

What is claimed is:

1. An image processing apparatus comprising:
a first feature value calculating section calculating, in an arbitrary region of an image obtained by picking up an image of a subject, a first feature value for each of pixels constituting the arbitrary region;
a region dividing section dividing the arbitrary region into multiple regions on the basis of the first feature values;
a second feature value calculating section calculating a second feature value for each region of the multiple regions divided by the region dividing section;
a classification section classifying each region of the multiple regions divided by the region dividing section into any of multiple kinds of attributes on the basis of the second feature value;
a diagnostic support information calculating section calculating an attribute value based on an area or a number, for each attribute of a same kind among the multiple kinds of attributes classified by the classification section;
a judgment section judging whether a region having a predetermined attribute exists or not among the multiple regions divided by the region dividing section; and
a correction section correcting, when it is judged by the judgment section that the region having the predetermined attribute exists, the attribute value for the region classified into the predetermined attribute on the basis of attribute values calculated for attributes other than the predetermined attribute, wherein
the diagnostic support information calculating section calculates diagnostic support information for supporting a diagnosis for the arbitrary region on the basis of the attribute value corrected by the correction section for the region having the predetermined attribute and the attribute values calculated by the diagnostic support information calculation section for the multiple regions other than the region having the predetermined attribute.

2. An image processing apparatus comprising:
a first feature value calculating section calculating, in an arbitrary region of an image obtained by picking up an image of a subject, a first feature value for each of pixels constituting the arbitrary region;
a region dividing section dividing the arbitrary region into multiple regions on the basis of the first feature values;
a second feature value calculating section calculating a second feature value for each of the regions divided by the region dividing section;
an attribute information storing section storing in advance each of pieces of attribute information about an attribute to be an indicator of a lesion with a high degree of malignancy, an attribute to be an indicator of a lesion with a low degree of malignancy and an attribute for which a benignancy and/or malignancy judgment is difficult to make;
a classification section classifying each of the regions divided by the region dividing section into any of the respective pieces of attribute information stored in the attribute information storing section on the basis of the second feature value calculated by the second feature value calculating section; and
a diagnostic support information calculating section calculating, for the arbitrary region, diagnostic support information for supporting a diagnosis, on the basis of rates of attributes classified by the classification section for each of the regions.

3. The image processing apparatus according to claim 1, further comprising an attribute information storing section storing in advance each of pieces of attribute information about an attribute to be an indicator of a lesion with a high degree of malignancy, an attribute to be an indicator of a lesion with a low degree of malignancy and an attribute for which a benignancy and/or malignancy judgment is difficult to make; wherein
the classification section classifies each of the regions divided by the region dividing section into any of the respective pieces of attribute information stored in the attribute information storing section on the basis of the second feature value calculated by the second feature value calculating section.

4. The image processing apparatus according to claim 1, wherein, when any of the multiple regions divided by the region dividing section includes a particular attribute to be an indicator of a remarkable degree of malignancy by the classification section, the diagnostic support information calculating section calculates the diagnostic support information on the basis of the particular attribute irrespective of attributes the other regions have.

5. The image processing apparatus according to claim 2, wherein
the attribute information storing section further stores attribute information about an attribute to be an indicator of a more remarkable degree of malignancy than the attribute to be an indicator of a lesion with a high degree of malignancy as the respective pieces of attribute information; and
when any of the multiple regions divided by the region dividing section includes the attribute to be an indicator of a remarkable degree of malignancy, the diagnostic support information calculating section calculates the diagnostic support information on the basis of the attribute to be an indicator of a remarkable degree of malignancy irrespective of attributes the other regions have.

6. The image processing apparatus according to claim 3, wherein
the attribute information storing section further stores attribute information about an attribute to be an indicator of a more remarkable degree of malignancy than the attribute to be an indicator of a lesion with a high degree of malignancy as the each piece of attribute information; and
when any of the multiple regions divided by the region dividing section includes the attribute to be an indicator of a remarkable degree of malignancy, the diagnostic support information calculating section calculates the diagnostic support information on the basis of the attribute to be an indicator of a remarkable degree of malignancy irrespective of attributes the other regions have.

7. The image processing apparatus according to claim 1, comprising a diagnostic support information storing section storing a range where the diagnostic support information, including a lesion name or a symptom name prepared in advance for the subject with the use of supervised data, exists in an N-dimensional virtual space corresponding to the multiple (N) kinds of attributes; wherein
the diagnostic support information calculating section calculates, from the attribute value calculated for each attribute of the same kind in the virtual space, the diagnostic support information corresponding to the attribute value.

* * * * *